(12) United States Patent
Kuperberg

(10) Patent No.: US 10,869,996 B2
(45) Date of Patent: Dec. 22, 2020

(54) METHOD AND APPARATUS FOR SEQUENTIAL DEPLOYMENT OF INTRA-TUMORAL AGENTS

(71) Applicant: Stephen Kuperberg, Winston Salem, NC (US)

(72) Inventor: Stephen Kuperberg, Winston Salem, NC (US)

(*) Notice: Subject to any disclaimer, the term of this patent is extended or adjusted under 35 U.S.C. 154(b) by 0 days.

(21) Appl. No.: 15/338,343

(22) Filed: Oct. 29, 2016

(65) Prior Publication Data

US 2020/0101272 A1  Apr. 2, 2020

(51) Int. Cl.
| A61M 31/00 | (2006.01) |
| A61B 17/3211 | (2006.01) |
| A61B 1/015 | (2006.01) |
| A61B 1/267 | (2006.01) |

(52) U.S. Cl.
CPC ........... *A61M 31/002* (2013.01); *A61B 1/015* (2013.01); *A61B 1/2676* (2013.01); *A61B 17/3211* (2013.01); *A61M 2210/1035* (2013.01); *A61M 2210/1039* (2013.01)

(58) Field of Classification Search
CPC ........ A61M 31/002; A61M 2210/1035; A61M 2210/1039; A61B 1/015; A61B 1/2676; A61B 17/3211
USPC .......................................................... 604/22
See application file for complete search history.

(56) References Cited

U.S. PATENT DOCUMENTS

| 5,267,960 | A | * | 12/1993 | Hayman | ............... | A61N 5/1027 |
| | | | | | | 600/3 |
| 5,868,741 | A | | 2/1999 | Chia et al. | | |
| 6,770,070 | B1 | | 8/2004 | Balbierz | | |
| 7,087,040 | B2 | | 8/2006 | McGuckin, Jr. et al. | | |
| 8,160,680 | B2 | | 4/2012 | Boyden et al. | | |
| 2009/0012201 | A1 | * | 1/2009 | Kim | ..................... | C08G 18/672 |
| | | | | | | 522/84 |
| 2009/0112201 | A1 | * | 4/2009 | Young | .................. | A61B 18/148 |
| | | | | | | 606/33 |
| 2014/0243664 | A1 | * | 8/2014 | El-Sayed | ............. | A61K 9/0009 |
| | | | | | | 600/431 |
| 2014/0350534 | A1 | | 11/2014 | Kircher et al. | | |
| 2014/0378906 | A1 | | 12/2014 | Fischell et al. | | |

FOREIGN PATENT DOCUMENTS

EP        2613704        7/2013

* cited by examiner

*Primary Examiner* — Phillip A Gray
(74) *Attorney, Agent, or Firm* — Patent Ventures, LLC

(57) ABSTRACT

An intra-tumoral agent deployment apparatus for diagnosing and delivering targeted, sequential deployment of agents to an endo-bronchial and, or an intra-parenchymal tumor, said apparatus formed of, among other things, an elongated shaft assembly including: at least one lumen; an intra-tumoral probe wire for tumor traversal, slidably interposed there between or slidably disposed between any one of, or combination of the at least one lumen; and wherein the displacement of the intra-tumoral probe wire causes disruption of an endo-bronchial and, or an intra-parenchymal tumor tissue, and, or creating an inlet for deployment of at least a first agent comprising any one of a therapeutic agent and, or a delivery vehicle from the first lumen, and a subsequent second agent comprising any one of a therapeutic agent and, or a binding agent from any one of the first lumen, second lumen, and, or the delivery vehicle.

19 Claims, 10 Drawing Sheets

METHOD AND APPARATUS FOR SEQUENTIAL DEPLOYMENT OF INTRA-TUMORAL AGENTS

BACKGROUND OF THE INVENTION

Field of Invention

The field of invention relates to a catheter and/or a device to diagnose and, or mechanically and/or chemically disrupt and/or break the tumor tissue in a lung for sequential deployment of agents, more particularly, to a device that causes displacement of an intra-tumoral probe wire interposed or slidably disposed between any one of a lumen further causing disruption of a tumor tissue and forming an inlet for local release of a therapeutic agent or a delivery vehicle from the first lumen and subsequently a release of a binding agent or a therapeutic agent from any one of the at least one lumens or the delivery vehicle, in order for longer retention and exposure of the therapeutic agent by the targeted tumor.

Related Art

Targeted therapy, specifically targeting lung cancer cells or tumor cells, is well established in the art. Targeted therapy in the context of lung cancer treatment usually refers to any mechanism intended to prevent the growth of cancer cells, or alternatively, to destroy them directly. Targeted therapy has significant advantages over standard chemotherapy: for one, it does not affect non-cancerous cells; and secondly, it does not result in the usual symptoms of nausea and fatigue associated with standard chemotherapy.

The vast majority of targeted therapy focuses on treatment on a molecular level: down-regulating or up-regulating genes that translate proteins involved in tumor growth. Some examples of such therapies are immunotherapies, apoptosis inducers, gene expression modulators, angiogenesis inhibitors, and signal transduction inhibitors. Immunotherapies, for example, entail stimulating the body's own immune system to target and attack the cancerous cells. The up-regulation of certain check-point inhibitors intended to block the PD-1 receptor—disrupt the signaling pathway involved in masking the tumor cells, and therefore, expose the tumor cell for an immune system attack.

This targeted approach plays well into the growing trend towards personalized medicine. Personalized medicine can be defined broadly as a model of healthcare that is predictive, personalized, preventive and participatory. Moreover, PM can also be referred to as the tailoring of medical treatment to the individual characteristics, needs and preferences of a patient during all stages of care, including prevention, diagnosis, treatment and follow-up. While PM and molecular-based targeted therapy have been traditionally associated with each other, there has been a void in ablation-based targeted therapy that is PM-focused.

While ablation-based targeted therapy is also known in the art, there is a void of any disclosure related to ablation-based targeted therapy with a sequential deployment of agents (therapy/delivery vehicle and therapy/binding agent). Additionally, there is void revolving dual lumen of personalized therapeutic agent and binding agent for more precise sequential deployment. The binding agent allows for increased retention and exposure of the therapy to the targeted tumor. Chia, et al. (U.S. Pat. No. 5,868,741) and Balbierz, et al. (U.S. Pat. No. 6,770,070) describes a catheter system for targeted ablation. Chia and Balbierz both describe an ablation mechanism entailing an ablation electrode at the distal end of the elongated member. Such an ablation electrode is not localized, nor does it describe a sequential deployment of a therapeutic and, or binding agent. Smith (EP 2613704) and Kircher, et al. (U.S. Ser. No. 14/184,934) describes a catheter apparatus with a distal end transducer—supporting a signal transduction pathway for localizing and targeting a tumor tissue. It, likewise, does not describe a mechanism for a revolving lumen arrangement or a sequential deployment of anti-tumor agents.

Boyden, et al. (U.S. Pat. No. 8,160,680) describes an instrument coupled to at least one energy source, sensor, and control circuit for targeted ablation. Additionally, Boyden teaches a rotatable instrument for increased tissue exposure, however, such rotation is not disposed within an elongated shaft of a catheter and does not mediate a sequential deployment of therapeutics. Fischell, et al. (U.S. Ser. No. 14/320,078) and McGuckin (7087040) each teach a tumor tissue ablation catheter having at least two shaft-encased lumens or lines for the purposes of achieving tissue penetration at varying depths. While sequential deployment may be achievable in the deployment arrangement taught by Fiscell or McGuckin, neither Fiscell nor McGuckin do not teach or suggest a sequential deployment of varying agents at a constant tissue depth or area.

SUMMARY

Sequential deployment of a first agent and then subsequently of a second agent, with or without the diagnostic guide, addresses the limitations of targeted ablation. Once targeted, the probe wire may be deployed for traversal of the tumor surface, and to further create a channel or inlet for the sequential deployment of tumor-treating agents. This ablation target becomes available for a sequential deployment of a therapeutic agent or a delivery vehicle and then a therapeutic agent or a binding agent. The binding agent may be any one of an agent that facilitates an increased retention and exposure of the therapeutic agent to the targeted tumor. The tumor may be of an endo-bronchial or intra-parenchymal nature, but not limited to such. The intra-tumoral apparatus may be used for tumors of all type, in any one of an anatomical region. However, usage in endo-brochial or intra-parenchymal tumors are best fitted given the novel functional features (sequential deployment) of the intra-tumoral deployment apparatus.

It is an object of the invention to disclose an intra-tumoral agent deployment apparatus, said apparatus comprising: an elongated shaft assembly including: a distal end portion with at least one port; at least one lumen axially disposed within the elongated shaft assembly, the at least one lumen extending through the shaft and engaged to the at least one port at the distal end; an intra-tumoral probe wire slidably interposed there between or slidably disposed between any one of, or combination of the at least one lumen.

Furthermore, it is also an object to comprise a proximal end housing a finger-led control coupled to an actuator, whereby said actuator is in operable communication to any one of, or combination of, the at least one port opening, protraction, retraction, and deployment of the intra-tumoral probe wire and, or a deployment line fittingly disposed between and, or within any of the at least one lumen, said deployment line operably coupled to for causing displacement of any one of the at least one port, and, or intra-tumoral probe wire, and any one of an agent; and wherein the displacement of the intra-tumoral probe wire interposed there between or slidably disposed between any one of, or combination of the at least one lumen causes disruption of a tumor tissue and forms an inlet for local deployment of a first agent and a second agent, whereby the first agent includes any one of a therapeutic agent and, or a delivery vehicle from the lumen, and subsequently a second agent including any one of a therapeutic agent and, or a binding agent from the lumen and, or the delivery vehicle. In such an embodiment, the lumens may be stationary and payload delivery is local—though not targeted to the probe-wire incision point. Additionally, a portion of the payload may be lost as a result of not entering the general vicinity of the probe point.

It is another object of the invention to disclose an ablation catheter comprising a rotatable lumen arrangement. Such an arrangement allows for a precise targeting of a tumor tissue for a sequential deployment of therapy or delivery vehicle and then a therapeutic agent or a binding agent. At least two lumens may be disposed within a rotatable cylinder that may be coupled to an electro-mechanical rotational means or strictly mechanical rotational means coupled to a proximally-housed actuator or driver. The cylinder may revolve around a central axis in the tubular member to bring each individual lumen and distal delivery port into alignment for precise and effective payload delivery.

The types and combination of agents that are sequentially deployed may be any one of therapeutic or a delivery vehicle first and then a binding agent or therapeutic agent as a subsequent agent. It is yet another object to disclose an invention, wherein the displacement of the intra-tumoral probe wire interposed there between or slidably disposed between any one of, or combination of the first and, or second lumen causes disruption of any one of a lung tumor tissue and, or lung lesion. Such a disruption may form an inlet for local displacement of a first agent including any one of, or combination of, a chemo-based, stem-cell based, immune-based, nano-based therapy, and, or a delivery vehicle from the first lumen and a second agent including any one of a binding agent or a therapeutic agent from any one of the first lumen, second lumen, or the delivery vehicle.

In another aspect of the invention, the intra-tumoral agent deployment apparatus may be stand-alone or slidably disposed within a tubular member of any one of a flexible or rigid bronchoscope or any one of a catheter, wherein the apparatus is configured to operate under any one of, or combination of, a control circuitry, control module, control unit, and, or control operator of any one of, or combination of the apparatus, and, or the bronchoscope. In accordance with the bronchoscope-fitted embodiment, the intra-tumoral agent deployment apparatus is slidably disposed within a tubular member of any one of a flexible or rigid bronchoscope, wherein the bronchoscope is configured to release the first agent from the first lumen of the apparatus and the second agent from the second lumen of the apparatus or the delivery vehicle, wherein the bronchoscope is configured to operate under any one of, or combination of, a control circuitry, control module, control unit, and, or control operator of any one of, or combination of the apparatus, and, or the bronchoscope. The intra-tumoral agent deployment apparatus may be fitted to a bronchoscope, wherein the bronchoscope guides the distal tip of the apparatus towards a tumor and, or lesion. With regard to endobronchial tumors, where entry of the catheter to deploy the agent into a tumor is inside the airway, probing may demand further probe manipulation in the way of rotation, protraction, and, or deployment of a surgical mesh field for increased channel size. However, for more sensitive intra parenchymal tumors, probe guidance by a fluoroscope, sonograph, or ultrasound may be necessary. It is crucial to avoid disruption of any blood vessels. The distal tip of any one of, or combination of, an apparatus, and, or a bronchoscope, may further comprise a fluoroscope, ultra-sound, or any other detection guide for confirmation of location of any one of a tumor, and, or a lesion. Moreover, further probe manipulation of the probe wire in the targeted tumor may not be advised, given the sensitivity and risks associated with such intra parenchymal tumors.

Other aspects and advantages of the invention will be apparent from the following description and the appended claims. It is to be understood that the foregoing general description and the following detailed description are exemplary and explanatory only, and are not necessarily restrictive of the disclosure. The accompanying drawings, which are incorporated in and constitute a part of the specification, illustrate subject matter of the disclosure and together with the general description, serve to explain the principles of the present disclosure. The disclosure will be understood by those skilled in the art from the following detailed description and drawings.

BRIEF DESCRIPTION OF DRAWINGS

The drawings illustrate the design and utility of embodiments of the present invention, in which similar elements are referred to by common reference numerals. In order to better appreciate the advantages and objects of the embodiments of the present invention, reference should be made to the accompanying drawings that illustrate these embodiments. However, the drawings depict only some embodiments of the invention, and should not be taken as limiting its scope. With this caveat, embodiments of the invention will be described and explained with additional specificity and detail through the use of the accompanying drawings in which.

DETAILED DESCRIPTION OF DRAWINGS

FIG. 1 is a side view of a distal portion, tubular member portion, and proximal portion of an intra-tumoral agent deployment mechanism according to an aspect of the invention. The present disclosure describes embodiments of an apparatus and methods in which a catheter itself or as part of a bronchoscope may be utilized to create an incision point into a specific area of targeted tumor in order to sequentially deploy a therapeutic agent or delivery vehicle and subsequently a binding agent or therapeutic into the precise target area. In some embodiments, the mechanisms for creating the incision point may be a lumen with a protracting distal-end point or probe wire. In some embodiments, an expandable sleeve is coated, impregnated, or embedded with collagenase, or any other tumor disrupting composition, for causing mechanical and chemical disruption. Additionally, sequential deployment may be accomplished by a tubular member disposed with a revolving lumen arrangement or a stationary lumen arrangement. In other embodiments, sequential deployment may be achieved by having a tubular member disposed with at least two lumens, each dedicated to a distinct tumor-disruptive agent. In yet other embodiments, a single lumen disposed within a tubular member may be dedicated to deploying two distinct tumor-disruptive agents in sequential fashion. Such sequential deployment has the effect of introducing the therapeutic agent or a delivery vehicle and then a binding agent or therapeutic agent. The delivery vehicle may be any one of, or combination of, a capsule, tablet, hydrogel, gel, liquid, and, or polymer. The binding agent may be any one of an agent causing increased retention and exposure of the therapeutic into the targeted tumor or a surgical wire mesh encapsulating the targeted tumor for achieving increased retention and exposure of the therapeutic agent into the targeted tumor.

Figure 1A:
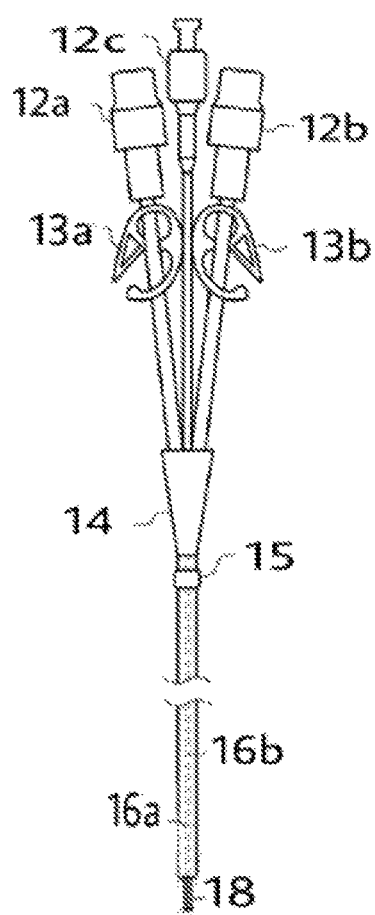
FIG. 1a is a top view of the intra-tumoral agent deployment apparatus according to an aspect of the invention.
Figure 1B:
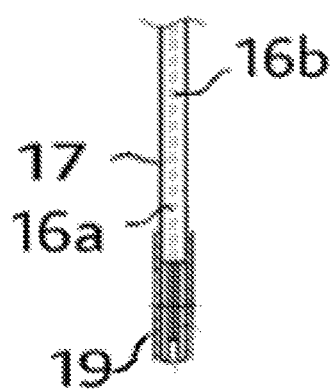
FIG. 1b is a close-up top view of the distal portion of the intra-tumoral agent deployment apparatus according to an aspect of the invention.

FIG. 1a and FIG. 1b illustrate an intra-tumoral agent deployment apparatus. FIG. 1a depicts a top perspective of the entire apparatus, while FIG. 1b depicts strictly the distal end of said apparatus. As FIG. 1a depicts, the apparatus comprises an elongated shaft assembly including: a distal end portion 17 with at least one port; at least one lumen 16(a), 16(b) axially disposed within the elongated shaft assembly, the at least one lumen 16(a), 16(b) extending through the shaft and engaged to the at least one port at the distal end 17; an intra-tumoral probe wire 18 slidably interposed there between or slidably disposed between any one of, or combination of the at least one lumen 16(a), 16(b); a proximal end housing a finger-led control coupled to an actuator, whereby said actuator is in operable communication to any one of, or combination of, the at least one port opening, protraction, retraction, and deployment of the intra-tumoral probe wire 18 and, or a deployment line fittingly disposed between and, or within any of the at least one lumen 16(a), 16(b), said deployment line operably coupled to and causing displacement of any one of the at least one port, and, or intra-tumoral probe wire 18, and any one of an agent; and wherein the displacement of the intra-tumoral probe wire 18 interposed there between or slidably disposed between any one of, or combination of the at least one lumen 16(a), 16(b) causes disruption of a tumor tissue and forms an inlet for local deployment of a first agent and a second agent, whereby the first agent includes any one of a therapeutic agent and, or delivery vehicle from a first lumen 16(a), 16(b), and subsequently a second agent including any one of a tumor binding agent and, or a therapeutic agent from any one of the first lumen 16(a), second lumen 16(b), and, or the delivery vehicle.

In another embodiment, the lumens may be housed within a rotatable cylinder. In such a rotating lumen embodiment, the apparatus is comprising of an elongated shaft assembly including a distal end portion with at least one port; a cylinder with any one of a electro-mechanical or mechanical rotational means and at least two fixed rotation points, such that each rotation point represents an alignment of any one of a lumen disposed within the cylinder with the distal end port; a first lumen axially disposed within the rotatable cylinder, said first lumen extending through the cylinder and engaged to a port at the distal end; a second lumen axially disposed within the rotatable cylinder, said second lumen extending through the cylinder and engaged to the port at the distal end; an intra-tumoral probe wire slidably interposed there between or slidably disposed between any one of, or combination of the first and, or second lumen. Furthermore, a proximal end housing a finger-led control may be coupled to an actuator, whereby said actuator is in operable communication to any one of, or combination of, a lumen port opening, and, or protraction, and, or retraction of the intra-tumoral probe wire and a deployment line fittingly disposed between and, or within any of the first lumen and, or the second lumen; a distal end housing a visual guide for the intra-tumoral probe wire; and wherein the displacement of the intra-tumoral probe wire interposed there between or slidably disposed between any one of, or combination of the first and, or second lumen causes disruption of any one of a lung tumor tissue and, or lung lesion and forms an inlet for local displacement of a first agent including any one of, or combination of, a chemo-based, stem-cell based, immune-based, nano-based therapy, and, or a delivery vehicle from the first lumen and subsequently a second agent including any one of a binding agent and, or a therapeutic agent from any one of the first lumen, second lumen, and, or the delivery vehicle.

In continuing reference to FIG. 1, the intra-tumoral agent deployment apparatus may further comprise at least one lumen 16(a), 16(b), each dedicated to delivery of a unique agent and, or a probe wire 18. The probe wire 18 may be interposed between the agent lumens 16(a), 16(b) or disposed within any one of, or both agent lumens 16(a), 16(b). Additionally, each lumen 16(a), 16(b) may be coupled to its dedicated luer 12(a), 12(b), 12(c) for control of agent or probe wire 18 positioning and delivery. Alternatively, a single lumen configuration may achieve sequential deployment by having the single lumen 16(a), 16(b) capable of compartmentalizing any one of agent 1, agent 2, and, or probe wire 18. In such a single lumen configuration, the probe wire 18 may be slidably adjacent to the single agent lumen 16(a), 16(b) or disposed within the single lumen 16(a), 16(b). Moreover, a single luer 12(a), 12(b), 12(c) may control positioning and delivery of any one of agent 1, agent 2, and, or probe wire 18.

While not shown in FIG. 1, a third lumen exclusive for housing the intra-tumoral probe wire may be provided. In such a configuration, wherein the probe wire may be in a dedicated lumen or tubular member amid the other agent-lumens, then each lumen may be coupled to its own respective lauer: luer 1 coupled to the first lumen with agent 1; luer 2 coupled to the second lumen with agent 2, and luer 3 coupled to the third lumen or middle lumen with the probe wire. Alternatively, the displacement mechanism for the agent-coupled lumen luers may be different from the probe wire-coupled lumen luer. In yet other embodiments, an actuator coupled to a deployment line may be the mechanism for displacing each of the two agents, along with the probe wire from the third lumen. In some embodiments, the deployment line may be in operable communication with pivotally-opposed arms at the distal end for actuating any one of, or combination of port openings, agent displacement, and, or protraction, and, or retraction of the intra-tumoral probe wire. The actuator may be the same or different between luer 1, 2, or 3.

The intra-tumoral agent deployment apparatus may further comprise a single deployment line disposed within any one of the first lumen, second lumen, and, or third lumen, and, or there between, wherein the single deployment line is in operable communication with pivotally-opposed arms at the distal end for actuating any one of, or combination of, port openings, agent displacement, and, or displacement of intra-tumoral probe wire.

In an embodiment, the proximal portion or housing portion is connected to the tubular member 15 through a hub 14 and the tubular members 15 proximal region is external to a patient and the tubular members 15 distal portion is internal to the patient and the proximal end of the proximal portion or delivery portion is connected to the distal end 17 of the tubular member 15. In other embodiments, the at least one or two, or three lauers 12(*a*), 12(*b*), 12(*c*) descend directly into the tubular member 15 portion. In some embodiments, the means for displacement comprises an actuator at a proximal end of the housing portion in communication via a channel with a means for displacement located in the delivery portion causing elastomeric expansion for mechanical disruption of the treated and bound tumor. The elastomeric portion on the delivery end may further comprise a plurality of traversable pores operable to achieve a controlled release of one or more tumor disrupting compositions. In yet other embodiments, the elastomeric portion may be embedded with collagenase, or any other chemically disruptive agent.

While not shown in FIG. 1, an elastomeric portion at the distal tip for mechanical disruption of a tumor may be composed of any one of a pliable, elastomeric composition (polyethylene, or neoprene, or any material that results from the polymerization of chloroprene). In some embodiments, the elastomeric portion is positioned in between the ports of a catheter apparatus. Direct or tangential strikes on a targeted tumor may provide the mechanical displacement necessary for supplementary disruption of the tumor tissue-ancillary to the sequential deployment of therapeutic/binding agent.

The actuator on the proximal end or housing portion may be a mechanical, optionally, electro-mechanical control which provides for precise, tensionable communication with a deployment line. Examples of a first actuator include, but are not limited to, an arm, lever, wheel unit, control stick, or control button—as a stand-alone or integrated as part of a luer. In one embodiment, a deployment line may be a wire line disposed within any one of a lumen, or between lumens, causing displacement of any one of, or combination of, a port opening, agent displacement, and, or probe wire. In other embodiments, deployment may be achieved via a controlled in-flow of a displacing agent. Displacing agents may be one or more of air, water, fluid, pneumatic, hydraulic, gas, or flowable agent that can fill the expanding tube and build pressure against the walls sufficient to displace the tube and sleeve. In an alternative embodiment, an expanding tube may be end-fitted with a longitudinal member coupled to pivotally opposable arms.

In a preferred embodiment, as depicted in FIG. 1*b*, the intra-tumoral agent deployment apparatus may, at a distal end 17 of the elongated shaft assembly, be further disposed with a tumor location guide or probe 19 for guiding the intra-tumoral probe wire 18. The tumor location guide 19 may be based on an ultrasound detection means and in electronic communication with a visual display at the proximal end or housing portion of the apparatus. Other visual guided techniques for guiding the intra-tumoral probe wire 18 may be used, such as sonography, fluoroscopy, etc.

Also not shown in FIG. 1, the intra-tumoral agent deployment apparatus may be slidably disposed within a tubular member of any one of a flexible or rigid bronchoscope, wherein the apparatus is configured to operate under any one of, or combination of, a control circuitry, control module, control unit, and, or control operator of any one of, or combination of the apparatus, and, or the bronchoscope. In integrated embodiments, the apparatus is integrated wholly with the bronchoscope, including the control commands. In other words, a physician may use the interface of the bronchoscope in order to control the positioning and deployment of the intra-tumoral agent deployment apparatus. In other embodiments, control commands will be shared, wherein a physician may interface with both the bronchoscope and apparatus in order to control position and deployment. In yet other embodiments, a physician may strictly interface with the apparatus for control and simply use the bronchoscope as a channel and gross guide.

In some embodiments, the bronchoscope is configured to release the first agent from the first lumen of the apparatus and the second agent from any one of the first lumen or second lumen of the apparatus, wherein the bronchoscope is configured to operate under any one of, or combination of, a control circuitry, control module, control unit, and, or control operator of any one of, or combination of the apparatus, and, or the bronchoscope.

In some embodiments, the visual guide or probe 19, such as the ultra-sound probe, fluoroscopic, or sonographic probe, may be coupled or disposed at a distal tip of the bronchoscope to guide the probe-wire. In other embodiments, the visual guide or probe 19 may be distally located on the bronchoscope-housed apparatus.

In some embodiments, probing of the tumor and sequential deployment of tumor-treating agents may be achieved by simply having stationary lumens 16(*a*), 16(*b*), each dedicated to a specific agent and, or probe wire 18. In such an embodiment, after probing is achieved and an inlet channel is traversed through a surface of a tumor, then agent 1 may be displaced from lumen 1 16(*a*) and agent 2 may then be displaced from any one of the lumen 116(*a*), lumen 2 16(*b*), or a delivery vehicle subsequent to the displacement of agent 1. Delivery vehicle may be any one of a capsule, tablet, hydrogel, gel, liquid, and, or polymer-based therapy vehicle. Due to the proximity of the lumens 16(*a*), 16(*b*) within the tubular assembly 15, the traversed tumor is bound to receive the majority of the therapeutic and binding agent payload. However, such a stationary lumen configuration may not be conducive to effectively delivering an entire payload intra-tumorally.

In other embodiments, while neither shown in FIG. 1*a*, nor 1*b*, the tubular member of the apparatus may further comprise a rotatable cylinder. The multiple lumens may be disposed within this rotatable cylinder. An electro-mechanical or mechanical means for rotating the cylinder may be located on the housing portion or proximal end. The rotation may be configured with three-fixed rotation points, each fixed rotation point representing the position of each respective lumens aligned with the tubular port. Each fixed rotation point may additionally be locked, so as to not risk displacing the probe wire or agent during non-alignment of lumen and tubular port. The cylinder may revolve around a central axis in the tubular member to bring each respective lumen and tubular port into alignment. This revolving cylinder configuration allows for precise agent delivery into the probe incision point of the tumor and greater payload delivery.

In continuing reference to the revolving cylinder configuration, a break-top housing on the proximal end (not shown in FIG. 1) may expose a loading gate, allowing for a physician to remove the lumens or reload the lumens. Releasing a lock and pushing the tubular member down exposes the lumens for convenient withdrawal and, or reloading. Alternatively, a swing-out cylinder mounted on a pivot co-axial with the lumens may be provided, whereby the cylinder swings out and down from the apparatus for lumen withdrawal and, or reloading.

Figure 2A:
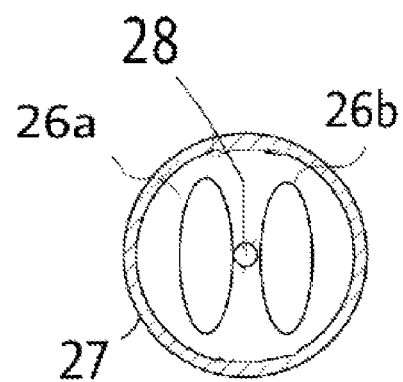
FIG. 2a is a front perspective of the distal end port opening of the intra-tumoral agent deployment apparatus according to an aspect of the invention.
Figure 2B:
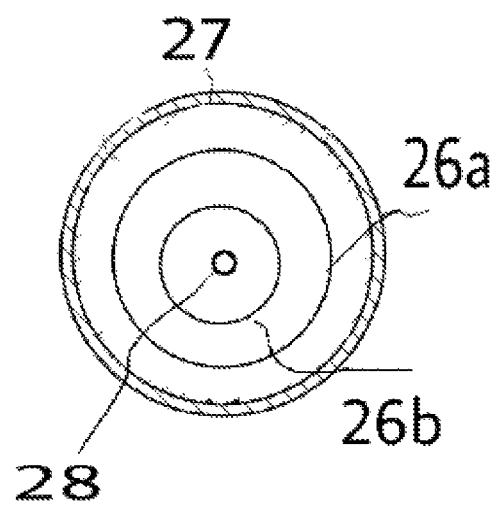
FIG. 2b is a front perspective of the distal end port opening of the intra-tumoral agent deployment apparatus according to an aspect of the invention.

Now in reference to FIGS. 2a and 2b. FIGS. 2a and 2b depict a close-up view of the distal delivery end of the intra-tumoral deployment apparatus. As FIG. 2a shows, an intra-tumoral probe wire 28 is slidably disposed between a dedicated lumen 26(a), 26(b). Alternatively, the intra-tumoral probe wire 28 may be interposed between the lumens 26(a), 26(b) and slidably disposed within the tubular member 27. In yet other embodiments, the probe wire 28 may be slidably disposed within a non-dedicated lumen 26(a), 26(b)—sharing the lumen 26(a), 26(b) with any one of the first deploying agent and, or the second deploying agent.

While not shown in FIG. 2, the proximal end housing may have at least one finger-led control coupled to at least one actuator, whereby said actuator is in operable communication to any one of, or combination of, the at least one port opening, protraction, retraction, and deployment of the intra-tumoral probe wire and, or a deployment line fittingly disposed between and, or within any of the at least one lumen, said deployment line operably coupled to and causing displacement of any one of an agent, at least one port, and, or intra-tumoral probe wire. In the dedicated lumen probe wire configuration, actuation may be achieved by a dedicated control or lauer. In other embodiments, actuation may be achieved by a universal or master control or lauer. In the non-dedicated lumen probe-wire configuration, probe-wire actuation may be achieved by a dedicated control or lauer. In yet other embodiments, probe-wire actuation may be achieved by dual functioning control or lauer, whereby the same control or lauer controls any one of an agent 1 and, or agent 2 deployment, along with probe-wire protraction and, or retraction.

The displacement of the intra-tumoral probe wire 28 interposed there between or slidably disposed between any one of, or combination of the at least one lumen 26(a), 26(b) causes disruption of a tumor tissue and forms an inlet for displacement of a first agent and then a second agent, whereby the first agent has a therapeutic agent, and the second agent has a tumor binding agent.

In some embodiments, probe-wire 28 protraction and, or retraction is caused by the mechanical or electro-mechanical displacement of the probe wire 28 through the sliding elongated member of a dedicated lumen 26(a), 26(b), non-dedicated lumen 26(a), 26(b), or tubular member 27 of the deployment apparatus. The mechanical or electro-mechanical force applied through the longitudinal member pushes or pulls the probe wire 28 out or in through the distal end of the tubular member 27. In other embodiments. In yet another embodiment, the protraction of the probe wire 28 may be caused by retracting the tubular member 27 relative to the probe wire 28 slidably disposed within the tubular member 27. Retracting of the tubular member 27 may be achieved by a control disposed on the proximal housing and coupled to a retracting actuator in communication with the tubular member 27.

While not shown in FIG. 2, guidance of the probe wire for targeted incision may be achieved by any one of imaging-linked probes, such as a fluoroscope, sonograph, or ultrasound probe. Once the area of interest is targeted, then the probe wire may first be deployed for an incision point on the area of target, followed by the sequential deployment of therapeutic agent or delivery vehicle and therapeutic agent or binding agent. As such, the apparatus may serve as a both a diagnostic tool with therapeutic delivery capability. In some instances, if nothing is visualized warranting a therapeutic response, then sequential deployment may not be necessary. The visual probes may be coupled directly on the apparatus, or utilize the visual probes fitted onto a bronchoscope.

The visual probe is sensitive in both "endobronchial" and "intra parenchymal" locations. Currently, intra parenchymal lesions are thought to be risky to approach. The visual probes may also identify the type of location, better informing the physician on invasive techniques. Perhaps, with the intra parenchymal lesions, the physician may decide to use the probe wire for incision, but with greater caution. Additionally, it may be best not to perform any further manipulation of the probe wire once an incision point is achieved. In other scenarios, wherein a less risky endobronchial lesion is visualized and targeted, post-incision manipulation of the probe wire may be advantageous to increase the size of the therapeutic channel.

In some embodiments (not shown), once probe-wire targeting has occurred and an incision point has been performed, post-incision manipulation of the probe wire may be advantageous. In such cases, an embodiment may allow for displacement of a pliable and pivotally opposable, inverted "V" shaped members at the distal end of the probe wire to protract out. Once the terminal ends of the members are completely free from the perimeter of the distal tip of the probe wire, the inverted "V" shaped members are fully expanded into an open state by tensile force. Once the probe wire is in the targeted tumor, the probe wire may be rotated for the inverted "V" shaped distal tip to create a larger therapeutic channel and then collapses back into the probe wire using the same interrelation of mechanical components and steps—in the inverted manner. In yet other embodiments, the inverted "V" shaped members may be fitted with a surgical mesh field to clear a wider are of the tissue field and create an even larger therapeutic channel. In an alternative embodiment of the invention, a collegenase-coated surgical wire mesh may also be used for added chemical disruption of the tissue field. Other cleaving agents such as pepsin or trypsin may additionally be used. The tumor may be of an endo-bronchial or intra-parenchymal nature, but not limited to such. The intra-tumoral apparatus may be used for tumors of all type, in any one of an anatomical region. However, usage in endo-brochial or intra-parenchymal tumors are best fitted given the novel functional features of the intra-tumoral deployment apparatus.

Now in reference to the therapeutic and binding agent housed in the lumens, the displacement mechanism causing displacement of the agents is an actuator at a proximal end of the tubular member in operable communication with a deployment line or tube fittingly received within a lumen. The deployment line or tube causes displacement of the agents by any one of, or combination of, pneumatic, hydraulic, electric, electromechanical (assisted), and manual (eg. a wire or "loading" component fed from the operational end through the scope through lumen and out of the port).

In continuing reference to FIG. 2a, probing of the tumor and sequential deployment of tumor-treating agents may be achieved by simply having stationary lumens 26(a), 26(b), each dedicated to a specific agent and, or probe wire 28. In such an embodiment, after probing is achieved and an inlet channel is traversed through a surface of a tumor, then agent 1 may be displaced from lumen 1 and agent 2 may then be displaced from lumen 1 26(a), lumen 2 26(b), or delivery vehicle subsequent to the displacement of agent 1. Due to the proximity of the lumens 26(a), 26(b) within the tubular assembly 27, the traversed tumor is bound to receive the majority of the therapeutic and binding agent payload. However, such a stationary lumen configuration may not be conducive to effectively delivering an entire payload intra-tumorally. In other embodiments, the probe-wire, agent 1, and agent 2 are all housed within the same lumen, so as to reduce the deployment radius and be more target specific. As FIG. 2b depicts, other embodiments call for a concentric lumen configuration, wherein lumen 1 26(a) encircles the probe wire 28 centrally disposed within the distal end of the tubular member 27, and lumen 2 26(b) encircles lumen 1 26(a).

Figure 3:
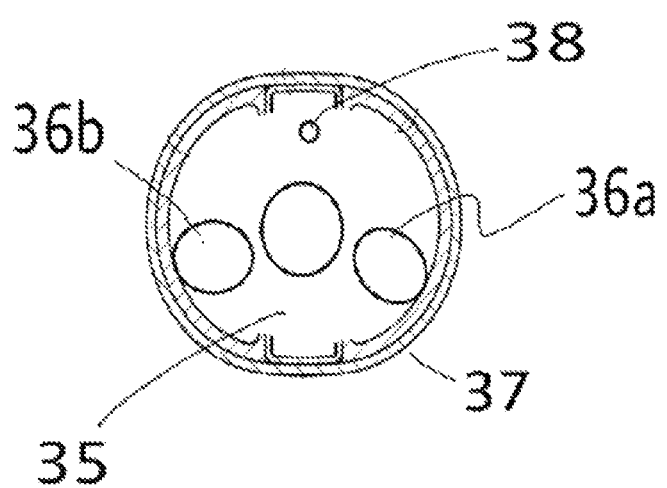
FIG. 3 is a front perspective of the distal end port opening of the intra-tumoral agent deployment apparatus with a revolving cylinder according to an aspect of the invention.

Now in reference to FIG. 3, the tubular member 37 of the apparatus may further comprise a rotatable cylinder 35. The multiple lumens 36(a), 36(b) may be disposed within this rotatable cylinder 35. An electro-mechanical or mechanical means for rotating the cylinder 35 may be located on the housing portion or proximal end. The rotation may be configured with three-fixed rotation points, each fixed rotation point representing the position of each respective lumens 36(a), 36(b) aligned with the tubular port. Each fixed rotation point may additionally be locked, so as to not risk displacing the probe wire 38 or agent during non-alignment of lumen 36(a), 36(b) and tubular port. The cylinder 35 may revolve around a central axis in the tubular member 37 to bring each respective lumen 36(a), 36(b) and tubular port into alignment. In other embodiments, the tubular member 37 itself may have the rotational means. In yet other embodiments, the lumens 36(a), 36(b) and, or probe wire 38 may have the rotational means. Rotational means may be achieved by having any one of, or combination of, the tubular member, cylinder, lumen/s, and, or intra-tumoral probe wire coupled to a mechanical, and, or electro-mechanical rotational means housed on a proximal end of the apparatus. Controls for rotation may be achieved by manipulation of a luer, joy-stick, button, arm, lever, located on a proximal top-end.

This revolving cylinder configuration shown in FIG. 3 allows for precise agent delivery into the probe incision point of the tumor and greater payload delivery. Such a revolving cylinder configuration guarantees an identical position and deployment radius for each and every deployment member. As such, there is even fewer risk of wastage compared to both the stationary lumen and concentric lumen configurations of FIG. 2a and FIG. 2b.

Though not shown FIGS. 2a, 2b, or 3, a single lumen may be provided, for housing all of the necessary components for sequential deployment: agent 1, agent 2, and, or the intra-tumoral probe wire. In other embodiments, the intra-tumoral probe wire may be adjacent to the single lumen. In yet other embodiments, three lumens may be provided: one lumen dedicated for each agent; and a third lumen for housing the intra-tumoral probe-wire.

Figure 4A:
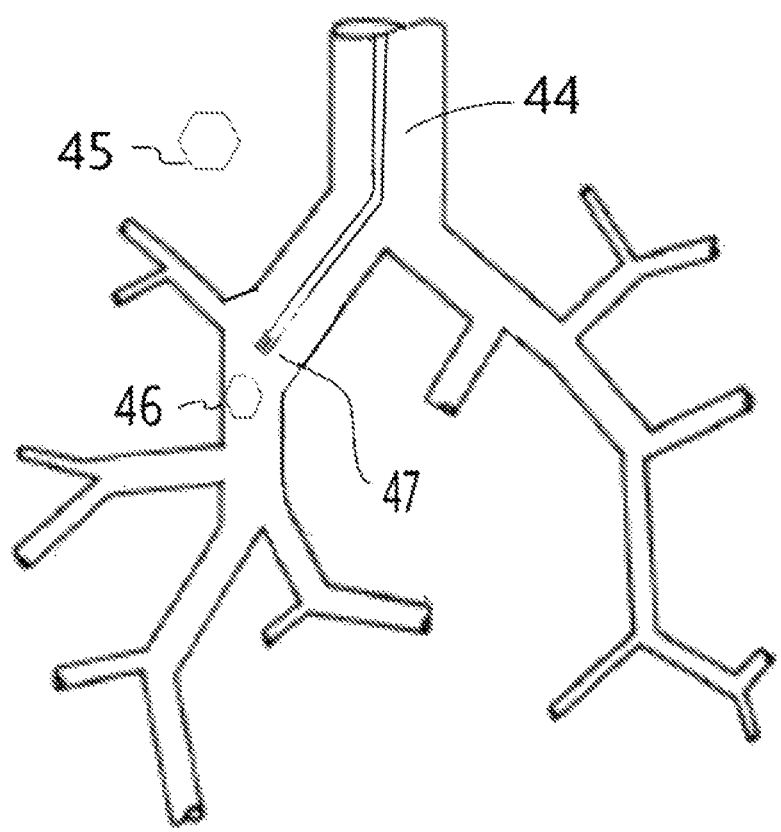
FIG. 4a is a schematic of a lung probing using the intra-tumoral agent deployment apparatus according to an aspect of the invention.
Figure 4B:
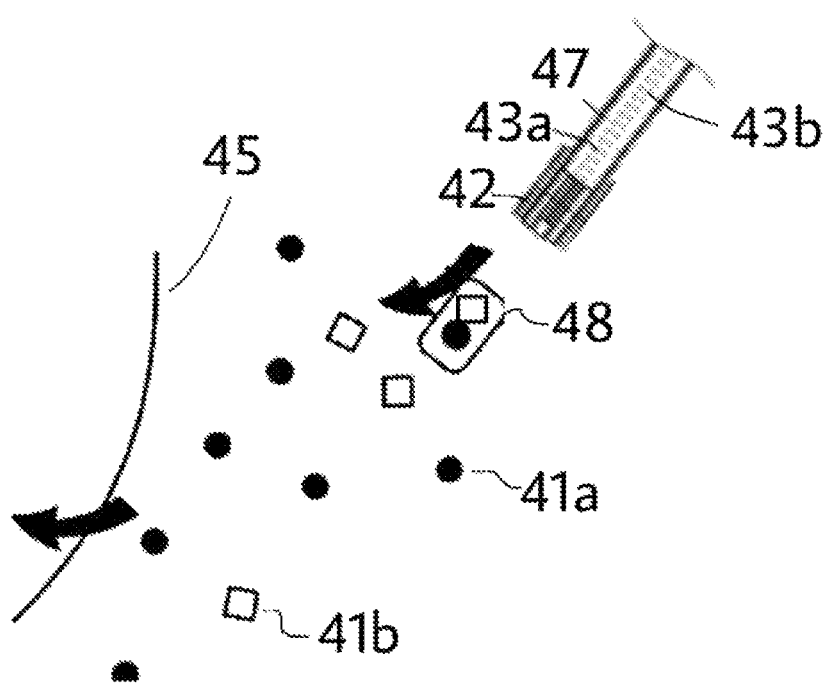
FIG. 4b is a schematic of a delivery agent deployed extra-tumorally from the intra-tumoral agent deployment apparatus according to an aspect of the invention.
Figure 4C:
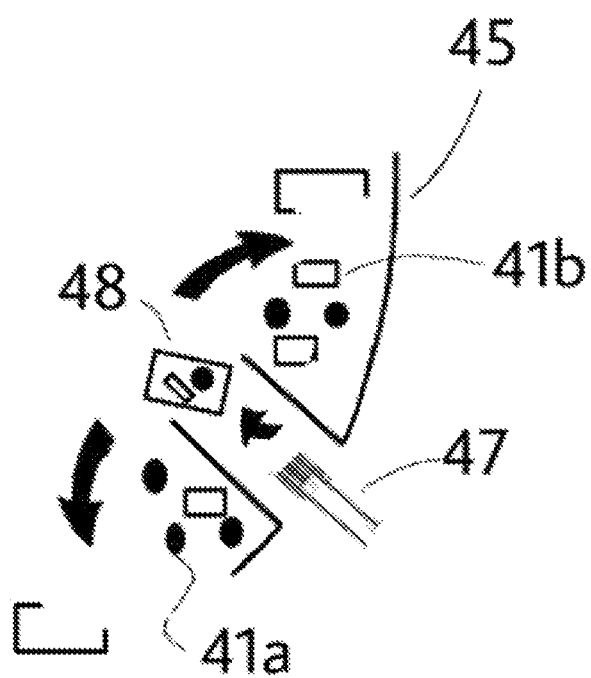
FIG. 4c is a schematic of a delivery agent deployed from the intra-tumoral agent deployment apparatus according to an aspect of the invention.

FIGS. 4a, 4b, and 4c illustrate the tumor striking dynamics of the intra-tumoral deployment apparatus. FIG. 4a represents an endo-bronchial tumor strike. Once the area of interest is targeted, then the probe wire may first be deployed for an incision point on the area of target, followed by the sequential deployment of therapeutic agent or delivery vehicle and therapeutic agent or binding agent. As such, the apparatus may serve as a both a diagnostic tool with therapeutic delivery capability. The visual probe is sensitive in both endo-brochial 45 and intra-parenchymal 46 locations. Currently, intra parenchymal 46 lesions are thought to be risky to approach. The visual probes may also identify the type of location, better informing the physician on invasive techniques. Perhaps, with the intra parenchymal 46 lesions, the physician may decide to use the probe wire for incision, but with greater caution. Additionally, it may be best not to perform any further manipulation of the probe wire once an incision point is achieved. In other scenarios, wherein a less risky endo-bronchial 45 lesion is visualized and targeted, as depicted in FIG. 4a, post-incision manipulation of the probe wire may be advantageous to increase the size of the therapeutic channel.

The first agent may be any one of a therapeutic agent with tumor-suppression/depletion efficacy or a delivery vehicle. Targeting may be achieved by a guide 42 disposed on the distal tip 47 of the apparatus. As FIGS. 4b and 4c both demonstrate, delivery vehicles 48 may be any one of a capsule, tablet, hydrogel, gel, liquid, and, or polymer—and deployed from any one of the first and, or second lumens 43(a), 43(b). There is then slow-acting release of the active therapeutic agent 41(a), 41(b) from the delivery vehicle intra-tumorally (4c) or extra-tumorally (4b), representing the second stage of a sequential deployment. This type of sequential deployment may occur endo-bronchially 45 and/or intra-parenchymally 45. In some embodiments, the therapeutic agent 41(a), 41(b) may be a chemotherapeutic agent, stem-cell therapeutic, immune-based therapeutic, or a nano-based therapeutic agent.

The second agent may be a tumor binding agent or yet another therapeutic agent 41(a), 41(b). In the case of FIGS. 4b and 4c, the second agent is deployed from the delivery vehicle 48 and may be any one of therapeutic agent, the deployment of which represents the second stage f the sequential deployment. In other embodiments, in cases where the first agent is not a delivery vehicle 48, the second agent may be any one of a therapeutic agent or binding agent-deployed from any one of the first and, or second lumens 43(a), 43(b). Binding agents are any agents that cause increased retention or exposure of the therapeutic agent within the targeted tumor. In some embodiments, tumor binding agents are agents capable of calcifying the tissue and prolonging the exposure of the first agent. In other embodiments, the binding agent may be a surgical mesh field that is configured to encapsulate the tumor body deployed from a lumen or any other distal end housing. The surgical mesh has the effect of increasing retention and exposure of the therapeutic agent in the targeted tumor. In some embodiments, any one of the first agent, and, or the second agent is a nano-based particle, whereby said particle is a carrier of any one of, or combination of, a chemo-based therapy, stem cell therapy, immuno-based therapy, nano-based therapy, and, or a tumor-binding agent. In yet other embodiments, the first agent may be any one of, or combination, of a chemo-based therapy, stem cell therapy, immune-based therapy, and, or a nano-based therapy. In yet other embodiments, the first agent being a delivery vehicle 48 such as a capsule, tablet, hydrogel, liquid, or other polymer or micelle in the case of a nano-based delivery.

In some embodiments, the apparatus and sequential deployment of agent 1 and agent 2 may be coupled to a Virtual Reality (VR) or Augmented Reality (AR) component. An apparatus or bronchoscope-fitted apparatus with visualization remotely connected by a Bluetooth-like device where the operator may be off site and visualizing the interior of the airway via the VR or AR glasses and operating via remote control may be possible. In the case of AR glasses, probe images may have an overlay of anatomical data to further guide the physician in any one of inserting the probe, manipulating the probe, deploying agent 1, and, or deploying agent 2.

Figure 5:
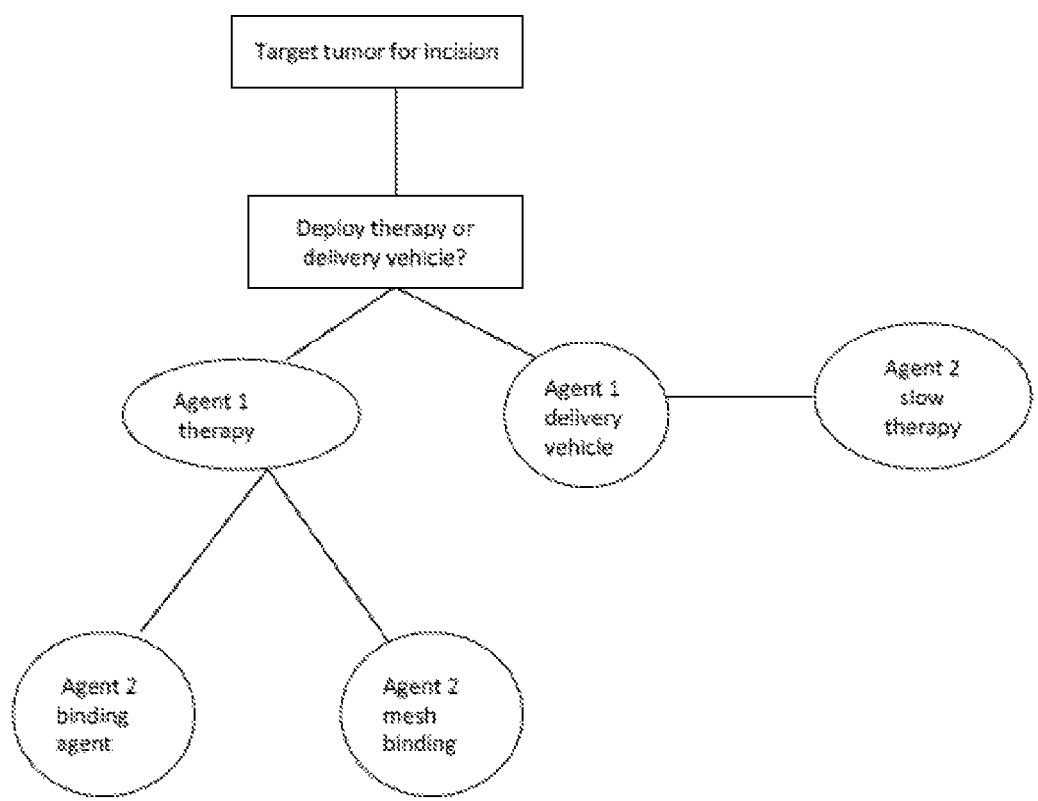
FIG. 5 is a process flow of the sequential deployment of a first agent and a second agent by the intra-tumoral deployment apparatus according to an aspect of the invention.

FIG. 5 illustrates a process flow of the sequential deployment from the intra-tumoral apparatus in accordance with an aspect of the invention. In a preferred embodiment agent 1 from lumen 1 may be therapeutic agent or a delivery vehicle. If agent 1 is a therapeutic agent, then agent 2 from lumen 1 and, or lumen 2 may be a binding agent. The binding agent may be any one of a surgical wire mesh configured for encasing the targeted tumor, or an agent for causing the calcification of the targeted tumor for increasing retention and exposure of the therapeutic agent 1 from lumen 1. If agent 1 is a delivery vehicle, such as a capsule, tablet, hydrogel, gel, liquid, and, or any polymer for transporting a therapeutic agent, then agent 2 may be a therapeutic agent slow-released from the delivery vehicle. In either scenario, agent 1 and agent 2 are sequentially deployed (agent 2 subsequent to agent 1) for a concerted tumor suppression or tumor depletion effort.

Figure 6:
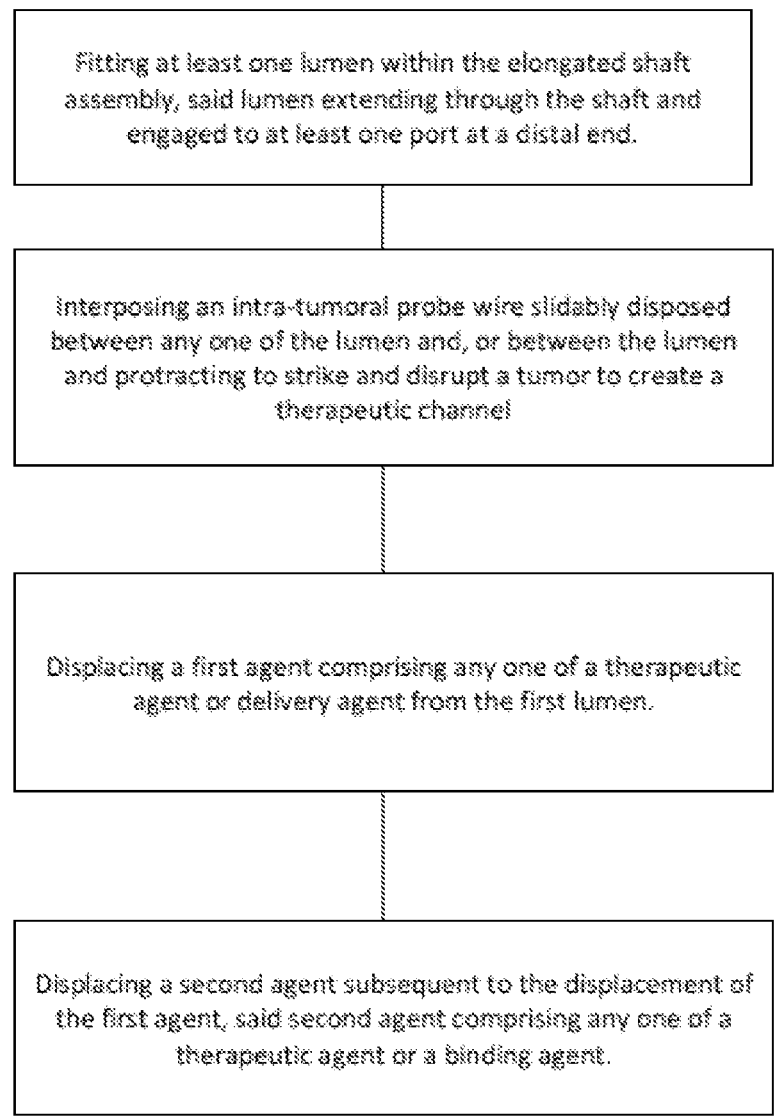
FIG. 6 is a method flow of the sequential deployment of a first agent and a second agent by the intra-tumoral deployment apparatus according to an aspect of the invention.

FIG. 6 illustrates a method flow of the sequential deployment from the intra-tumoral apparatus in accordance with an aspect of the invention. said method comprising the steps of: (1) fitting at least one lumen axially within the elongated shaft assembly, said first lumen extending through the shaft and engaged to at least one port at the distal end; (2) interposing an intra-tumoral probe wire slidably disposed within or between any one of the lumen; (3) coupling a proximal end housing with a finger-led control to an actuator, whereby said actuator is in operable communication to any one of, or combination of, the lumen port opening, protraction, and, or retraction of the intra-tumoral probe wire and a deployment line fittingly disposed between and, or within any of the lumen, said deployment line operably coupled for causing displacement of any one of the lumen port, intra-tumoral probe wire, and, or agent displacement; and (4) disrupting a tumor tissue and forming an inlet for local displacement of a first agent including any one of, or combination of, a therapeutic agent and, or a delivery vehicle from the lumen and a subsequent second agent including any one of, or combination of, a therapeutic agent and, or a binding agent from any one of the lumen and, or the delivery vehicle.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of the invention.

Unless otherwise defined, all terms used in disclosing embodiments of the invention, including technical and scientific terms, have the same meaning as commonly understood by one of ordinary skill in the art to which this invention belongs, and are not necessarily limited to the specific definitions known at the time of the present invention being described. Accordingly, these terms can include equivalent terms that are created after such time. It will be further understood that terms, such as those defined in commonly used dictionaries, should be interpreted as having a meaning that is consistent with their meaning in the present specification and in the context of the relevant art and will not be interpreted in an idealized or overly formal sense unless expressly so defined herein. All publications, patent applications, patents, and other references mentioned herein are incorporated by reference in their entirety.

In the above description, for purposes of explanation, numerous specific details are set forth in order to provide a thorough understanding of the invention. It will be apparent, however, to one skilled in the art that the invention can be practiced without some specific details. Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments. Although a few exemplary embodiments of the present disclosure have been shown and described, the present disclosure is not limited to the described exemplary embodiments. Instead, it would be appreciated by those skilled in the art that changes may be made to these exemplary embodiments without departing from the principles and spirit of the present disclosure, the scope of which is defined by the claims and their equivalents.

I claim:

1. An apparatus for sequential deployment of intra-tumoral agents, said apparatus comprising:
   an elongated shaft assembly including:
   a distal end portion with at least one port opening;
   at least a first and second lumen axially disposed within the elongated shaft assembly, the at least first and second lumen extending through the shaft and engaged to the at least one port opening at the distal end, wherein the first lumen comprises a therapeutic agent for deployment and the second lumen comprises a binding agent for subsequent deployment;
   an intra-tumoral probe wire slidably interposed there between or slidably disposed between any one of, or combination of the at least first and second lumen;

a proximal end housing a finger-led control coupled to an actuator, whereby said actuator is in operable communication to any one of, or combination of, the at least one port opening, protraction, retraction, and deployment of the intra-tumoral probe wire and, or a deployment line fittingly disposed between and, or within any of the at least first and second lumen, said deployment line operably coupled to and causing displacement of any one of an agent, at least one port, and, or intra-tumoral probe wire; and wherein the displacement of the intra-tumoral probe wire interposed there between or slidably disposed between any one of, or combination of, the at least first and second lumen causes disruption of a tumor tissue and forms an inlet for displacement of a first agent comprising any one of a therapeutic agent from the first lumen and a subsequently deployed second agent comprising any one of a binding agent from the second lumen, wherein the binding agent encapsulates and/or calcifies the tumor for prolonged exposure of the tumor to the therapeutic agent.

2. The sequential intra-tumoral agent deployment apparatus of claim 1 further comprising a third lumen for housing the intra-tumoral probe wire and at least one of a therapeutic agent and/or binding: agent.

3. The sequential intra-tumoral agent deployment apparatus of claim 1 further comprising a single deployment line disposed within at least one of the first lumen, second lumen, and, or there between, wherein the single deployment line is in operable communication with pivotally-opposed arms at the distal end for actuating any one of, or combination of, port openings or displacement of intra-tumoral probe wire.

4. The sequential intra-tumoral agent deployment apparatus of claim 1, wherein the distal end of the elongated shaft assembly is further disposed with a tumor location guide.

5. The sequential intra-tumoral agent deployment apparatus of claim 4, wherein the tumor location guide uses ultrasound detection for locating the tumor and guiding the intra-tumoral probe wire.

6. The sequential intra-tumoral agent deployment apparatus of claim 1, wherein said apparatus is slidably disposed within a tubular member of any one of a flexible or rigid bronchoscope, wherein the apparatus is configured to operate under any one of, or combination of, a control circuitry, control module, control unit, and, or control operator of any one of, or combination of the apparatus or the bronchoscope.

7. The sequential intra-tumoral agent deployment apparatus of claim 1, wherein said apparatus is slidably disposed within a tubular member of any one of a flexible or rigid bronchoscope, wherein the bronchoscope is configured to release the first agent from the first lumen of the apparatus and the second agent from the second lumen of the apparatus, wherein the bronchoscope is configured to operate under any one of, or combination of, a control circuitry, control module, control unit, and, or control operator of any one of, or combination of the apparatus or the bronchoscope.

8. The sequential intra-tumoral agent deployment apparatus of claim 6, wherein the bronchoscope guides the distal tip of the apparatus towards at least one of a tumor or lesion.

9. The sequential intra-tumoral agent deployment apparatus of claim 1, wherein the distal tip of any one of, or combination of, the apparatus or a bronchoscope further comprises a fluoroscope for confirmation of location of any one of a tumor or a lesion.

10. The sequential intra-tumoral agent deployment apparatus of claim 1, wherein the first agent is any one of, or combination of $_f$ a chemotherapeutic agent, stem-cell therapeutic agent, immune-based therapeutic agent, or nano-based therapeutic agent including any one of dendrimers, micelles or nanotubes.

11. The sequential intra-tumoral agent deployment apparatus of claim 1, wherein any one of the first agent, and, or the second agent is a nano-based particle, whereby said particle is a carrier of any one of, or combination of, a chemo-based therapy, stem cell therapy, immuno-based therapy, nano-based therapy or a binding agent.

12. The sequential intra-tumoral agent deployment apparatus of claim 1, wherein at least two lumens are rotatably disposed within the elongated shaft assembly, whereby the first lumen with the first agent is subsequently interposed with the second lumen with the second agent to produce a sequential deployment of the first agent and then the second agent at a same ablation target.

13. The sequential intra-tumoral agent deployment apparatus of claim 10; wherein a delivery vehicle with the therapeutic agent, such as a capsule, tablet, hydrogel, liquid, and, or other polymer delivering the therapeutic agent; and a second deployment being a slow-acting release of the therapeutic agent from the delivery vehicle.

14. The sequential intra-tumoral agent deployment apparatus of claim 10, wherein a first deployment being the therapeutic agent from a lumen; and a second deployment being a binding agent from any one of the same lumen and the second lumen, whereby the binding agent calcifies the tumor for prolonged exposure of the therapeutic agent.

15. The sequential intra-tumoral agent deployment apparatus of claim 10, wherein a first deployment being the therapeutic agent from a lumen; and a second deployment being a binding agent from any one of the same lumen and the second lumen, whereby the binding agent is a surgical wire mesh to encapsulate the tumor and prolong exposure of the therapeutic agent.

16. The sequential intra-tumoral agent deployment apparatus of claim 1, wherein any one of targeting, probing, and, or sequential deployment of the first agent and the second agent is directed toward an endo-bronchial or intra-parenchymal tumor.

17. A method of sequentially deploying intra-tumoral agents, said method comprising the steps of:
fitting at least a first and second lumen axially within the elongated shaft assembly, said first and second lumen extending through the shaft and engaged to at least one port at the distal end;
interposing an intra-tumoral probe wire slidably disposed within or between each of the first and second lumen;
coupling a proximal end housing with a finger-led control to an actuator, whereby said actuator is in operable communication to any one of, or combination of, each lumen port opening, protraction, and, or retraction of the intra-tumoral probe wire and a deployment line fittingly disposed between and, or within each of the at least first and second lumen, said deployment line operably coupled for causing displacement of any one of the lumen port, intra-tumoral probe wire, and, or agent displacement; and
disrupting a tumor and forming an inlet for local displacement of a first agent comprising a therapeutic agent from the first lumen and a subsequent deployed second agent comprising a binding agent from the second lumen, wherein the binding agent encapsulates and/or calcifies the tumor for prolonged exposure of the tumor to the therapeutic agent.

18. The method of claim 17, wherein the first agent is any one of, or combination of, a chemo-based, stem-cell based, immune-based, and, or nano-based therapy, within or without a delivery vehicle, from the first lumen and the subsequently deployed second agent is any one of a binding agent from the second lumen.

19. A method for sequentially deploying intra-tumoral agents, said method comprising the steps of:
   displacing an intra-tumoral probe wire interposed or slidably disposed between or within at least a first lumen and a second lumen; and
   causing disruption of a tumor and forming an inlet for displacement of a first therapeutic agent comprising at least one of a chemo-based, stem-cell based, immune-based, ora nano-based therapy from the first lumen and a subsequent second binding agent comprising at least one of a calcifying or encapsulating agent from the second lumen for prolonging exposure of the tumor to the therapeutic agent for increased efficacy.

\* \* \* \* \*